(12) United States Patent
Chen et al.

(10) Patent No.: US 6,610,302 B1
(45) Date of Patent: Aug. 26, 2003

(54) ANTI-TUMOR ACTIVITY OF EA-2 AND EA-4-PEPTIDE OF PRO-IGF-I

(75) Inventors: Thomas T. Chen, Storrs, CT (US); Maria J. M. Chen, Storrs, CT (US)

(73) Assignee: University of Connecticut, Storrs, CT (US)

( * ) Notice: Subject to any disclaimer, the term of this patent is extended or adjusted under 35 U.S.C. 154(b) by 0 days.

(21) Appl. No.: 09/669,642

(22) Filed: Sep. 26, 2000

Related U.S. Application Data

(63) Continuation-in-part of application No. 09/120,818, filed on Jul. 22, 1998, now Pat. No. 6,358,916.

(51) Int. Cl.[7] .............................................. A61K 39/00
(52) U.S. Cl. ........................ 424/198.1; 514/12; 530/399
(58) Field of Search .................................. 530/350, 399; 514/12; 424/85.2, 198.1

(56) References Cited

U.S. PATENT DOCUMENTS

| | | | |
|---|---|---|---|
| 5,093,317 A | 3/1992 | Lewis et al. | .................. 514/12 |
| 5,476,779 A | 12/1995 | Chen et al. | .............. 435/240.1 |

FOREIGN PATENT DOCUMENTS

| | | |
|---|---|---|
| EP | 0 309 050 A1 | 3/1989 |
| WO | WO 89/05822 | 6/1989 |
| WO | WO 93/23067 | 11/1993 |

OTHER PUBLICATIONS

Siegfried et al., PNAS, 89:8107–8111, Sep. 1992.*
Zheng, J.L. et al., "Induction of Cell Proliferation by Fibroblast and Insulin–Like Growth Factors in Pure Rat Inner Ear Epithelial Cell Cultures," *J. Neurosci.* 17 (*1*): 216–226 (Jan. 1, 1997) (XP–002060020).
Cambrey, A.D. et al., "Insulin–like growth factor I is a major fibroblast mitogen produced by primary cultures of human airway epithelial cells," *Clinical Science* 89:611–617 (1995).
Duguay, S.J. et al., "Mutational Analysis of the Insulin–like Growth Factor I Prohormone Processing Site," *J. of Biol. Chem.* 270(29):17566–17574 (1995).
Duguay, S.J. et al., "Nucleotide Sequence and Tissue Distribution of Three Insulin–Like Growth Factor I Prohormones in Salmon," *Molecular Endocrinology*, 6(8):1202–1210 (1992).
Greene, M.W. and Chen, T.T., Temporal expression pattern of insulin–like growth factor mRNA during embryonic development in a teleost, rainbow trout (*Onchorynchus mykiss*), *Mol. Marine Biol. and Biotech.* 6(2):144–151 (1997).
Hylka, V.W. and Straus, D.S., "The E–domain peptide of rat pro–insulin–like growth factor II (proIGF–II): properties of the peptide in serum and production by rat cell lines," *Biochimica et Biophysica Acta* 1051:6–13 (1990).
Siegfried, J.M. et al., "A mitogenic peptide amide encoded within the E peptide domain of the insulin–like growth factor IB prohormone," *Proc. Natl. Acad. Sci. USA* 89:8107–8111 (1992).
Shamblott M.J. and Chen, T.T., "Age–related and tissue–specific levels of five forms of insulin–like growth factor mRNA in a teleost," *Mol. Marine Biol. and Biotech.* 2(6):351–361 (1993).
Wallis, A.E. and Devlin, R.H., "Duplicate Insulin–Like Growth Factor–I Genes in Salmon Display Alternative Splicing Pathways," *Mol. Endocrinology* 7(3):409–422 (1993).
International Search Report dated Dec. 11, 1999 for International Application No. PCT/US99/16797.
Roberts, et al., "Molecular Cloning of Rat Insulin–Like Growth Factor I Complementary Deoxyribonucleic Acids: Differential Messenger Ribonucleic Acid Processing and Regulation by Growth Hormone in Extrahepatic Tissues," *Mol. Endocrinology* 1(3): 243–248 (1987).
Nagaoka, et al., "Expression of insulin–like growth factor–IA and factor–IB mRNA in human liver, hepatoma cells, macrophage–like cells and fibroblasts," *Federation of European Biomedical Societies*, 280(1), 79–83 (Mar. 1991).

* cited by examiner

*Primary Examiner*—Lorraine Spector
*Assistant Examiner*—Eileen B. O'Hara
(74) *Attorney, Agent, or Firm*—Cummings & Lockwood

(57) ABSTRACT

Compositions of pro-IFG-I E-peptides for the treatment and amelioration of tumor-producing diseases, and methods for their utilization.

7 Claims, 9 Drawing Sheets

Magnification: 10 x 20

Fig. 7. Effect of Ea-4-peptide on the invasion activity of HT-1080 cells[1]

| Treatment | # invaded cells/view (MIC[2]) | # invaded cells/view (CIC[3]) | % invasion[4] |
|---|---|---|---|
| No Ea-4-peptide | 63±13 | 157±6 | 40% |
| Control protein | 62±5 | 157±6 | 39% |
| Ea-4-peptide (4.2 nM) | 30±5 | 157±6 | 19% |
| Ea-4-peptide (8.4 nM) | 24±1 | 157±6 | 15% |

[1]Invasive assay was conducted in BIOCOAT MATRIGEL Invasion chambers following the procedure provided by Becton Dickinson Labware (Bedford, MA; 40480 and 40481 guidelines).

[2]MIC, Mean number of invaded cells per view invaded through Matrigel insert membrane. Each cell number is determined by averaging three independent counting ± deviation of the mean.

[3]CIC, Mean number of cells per view migrated through control insert membrane. Each cell number is determined by averaging three independent counting + deviation of the mean.

[4]% invasion = $\dfrac{\text{Mean \# of cells invading through Matrigel insert membrane}}{\text{Mean \# of cells migrating through control insert membrane}} \times 100$

Figure 7

ANTI-TUMOR ACTIVITY OF EA-2 AND EA-4-PEPTIDE OF PRO-IGF-I

CROSS-REFERENCE TO RELATED APPLICATIONS

This application is a continuation-in-part application of U.S. patent application Ser. No. 09/120,818, filed Jul. 22, 1998, now U.S. Pat. No. 6,358,916, the disclosure of which is hereby incorporated in its entirety.

GOVERNMENT SUPPORT

The invention was supported, in whole or in part, by grant number 9596241 from the National Science Foundation. The U.S. Government has certain rights in the invention.

BACKGROUND OF THE INVENTION

1. Field of the Invention

The present invention generally relates to anti-tumor peptides. In particular, the present invention relates to use of specified pro-IGF-1-peptides in the treatment and amelioration of tumor-producing diseases. Certain pro-IGF-1-peptides are shown to decrease tumor growth and to reduce metastasis.

2. Brief Description of the Related Art

Attention recently has been focused on the biological activities of the proteolytically-processed polypeptides from post-translational modified peptide hormones. For example, the C-peptide of pro-insulin has long been regarded to be biologically inactive except for a possible role in the folding of the insulin molecule during its post-translational modification. However, Ito et al. (14) have found recently that the C-peptide of pro-insulin is important in restoring vascular and neural dysfunction and $Na^+/K^+$-dependent ATPase activity in diabetic rats. Although a synthetic peptide amide of human b-type IGF-I E-peptide has been shown to exert mitogenic activity by Sieffied et al. (5), the biological activity of the native human E-peptides have not been identified.

Insulin-like growth factor-I (IGF-I) is a member of the insulin gene family and plays an essential role in growth, differentiation, regeneration and metabolism in all vertebrates (2). In all animals studied to-date, the primary translation product of IGF-I mRNA contains distinct regions or domains, including an N-terminal pre-peptide leader, followed by the mature peptide with B, C, A and D domains, and a C-terminus E domain. Due to alternative RNA splicing, two different forms, the a- and b-type, of IGF-I pro-hormones exist in mammals, differing only in the E-peptide region. In human, mouse and rat, the first 15 amino acid residues in the N-termini of the E-peptides of pro-IGF-Ia and -Ib share identical sequences, and this region is referred to as the common region. The sub-types of pro-IGF-I's are distinguished from one another by the amino acid sequences after the first 15 common amino acids, known as the variable regions of the E-peptides (3).

In mammals, the signal peptide and the E-peptide are proteolytically cleaved after translation from the pre-pro-hormone to form a mature peptide of 70 amino acid residues. The E-peptides of mammalian pro-insulin-like growth factor-I (pro-IGF-I) have long been regarded as biologically inactive.

Surprisingly, the present inventors have recently discovered that certain recombinant rainbow trout pro-IGF-I E-peptides (Ea-2-, Ea-3- and Ea-4), like hIGF-1, exhibit a dose-related mitogenic activity in several mammalian cell lines (Tian et al. (1)).

Four different forms of a-type IGF-I mRNA have been observed in rainbow trout (rt), *Oncorhynchus mykiss*, and are designated as IGF-I Ea-1, Ea-2, Ea-3 and Ea-4 (4). Nucleotide sequence comparison of the four size forms of IGF-I mRNAs reveal that the size differences among these mRNA species are due to insertions or deletions in the E domain regions of the molecules. The first 15 predicted amino acid residues of the four E-peptides share identical sequences among themselves as well as with pro-IGF-I E-peptides of human, mouse, and rat. The presence of the C-terminal 20 amino acid residues, sharing 70% identity with their human counterparts, identifies them to the a-type E-peptides.

The Ea-1-peptide of the rt-pro-IGF-I is a polypeptide of 35 amino acid residues, comprising the first 15 and the last 20 amino acid residues. Ea-2 and Ea-3 peptides differ from Ea-1 by virtue of either a 12- or 27-amino acid residue insertion between the first and last segments of the Ea-1-peptide sequence, respectively, while Ea-4 contains both insertions. The predicted numbers of amino acid residues in each E-peptide are, thus, 35, 47, 62 and 74, respectively. There has not been any report on the presence of b-type IGF-I mRNA in rainbow trout.

While the biological functions of the mature IGF-I peptide have been intensively studied, the functions of E-peptides have been overlooked and remain to be identified.

Siegfried et al. (5) have recently shown that the amide of a 22-amino acid residue encoded within the variable region of the E-peptide of the human IGF-Ib ($IBE_1$) exerts mitogenic activity in normal and malignant bronchial epithelial cells. Surprisingly, as set forth above, the present inventors have recently found that certain E-peptides from fish possess mitogenic activity with respect to mammalian cells (Tian et al. (1) report that recombinant rainbow trout Ea-2-, Ea-3- and Ea-4-peptide possess mitogenic activity in several normal and oncogenic transformed mammalian cell lines including NIH 3T3 cells, human embryonic kidney cells transformed by retrovirus (293GP), human mammary gland tumor cells (MCF-7) and caprine mammary epithelium cells (CMEC) (6)).

Based on the surprising inter-class activity of icthyofauna Pro-IGF-I E-peptides on mammalian cells, and given that trout Ea-2, Ea-3 and Ea-4 peptides containing a signal motif for peptidyl C-terminal amidation (4,7) and a bipartite consensus nuclear localization sequence (4,8), the present inventors hypothesized that these peptides might possess other novel biological activities on mammalian cells. In its screening for novel biological activities of trout pro-IGF-I E-peptides, the present inventors undertook several studies of the effects of such E-peptides on morphology, colony formation activity on a soft agar medium, and invasiveness of human and trout cancer cells. Surprising and unexpected anti-tumor activity was discovered.

SUMMARY OF THE INVENTION

The present provides a method for reducing tumor growth and the invasiveness of cancerous cells in mammals and fish by administration of a Pro-IGF-I E-peptide obtained from fish.

The present inventors have shown that the treatment of established human and fish cancer cell lines (MCF-7; HT-29; HepG2, ZR-75-1, SK-N-F1 and HC) and an oncogenic transformed human cell line (293GP) with recombinant trout Ea-2- or Ea-4-, but not Ea-3-peptide, resulted in a dose-dependent induction of morphological change and enhanced cell attachment. They have also shown that the in vitro colony formation activity of the oncogenic transformed cell line or established tumor cell lines is greatly reduced or diminished by treatment with the trout Ea-4-peptide. Furthermore, the invasive activity of HT1080, a known invasive cancer cell line, is also reduced many fold by treatment with the Ea-4-peptide. These results suggest that the Ea-4- and Ea-2-peptides of rainbow trout pro-IGF-I are able to control the malignant properties of cancer cells. The E-peptide-induced morphological changes are sensitive to treatment with α-amanitin or cycloheximide, known inhibitors of RNA and protein synthesis.

In one embodiment of the present invention there is disclosed a method of inhibiting proliferation of malignant cells, comprising administering to the malignant cell at least one E-domain peptide agent. The E-domain peptide agent is preferably selected from the group consisting of: a trout E-domain peptide, an E-domain peptide homolog, and an E-domain peptide fusion protein, and may more preferably be an E-domain peptide of a rainbow trout. In a preferred embodiment, trout E-domain peptide is selected from the group consisting of: Ea-2 domain peptide (SEQ ID NO:2) and Ea-4 domain peptide (SEQ ID NO:4). The E-domain peptide agent may be administered in a pharmaceutical composition.

In another embodiment of the present invention, there is disclosed method of inhibiting the proliferation of malignant cells, comprising administering to the malignant cells a nucleic acid encoding an E-domain peptide agent. Preferably the E-domain peptide agent is selected from the group consisting of: a trout E-domain peptide, an E-domain peptide homolog, and an E-domain peptide fusion protein.and more preferably the E-domain peptide is an E-domain peptide of a rainbow trout, in particular having a sequence selected from the group consisting of: Ea-2 domain peptide (SEQ ID NO:2) and Ea-4 domain peptide (SEQ ID NO:4). The nucleic acid encoding the E-domain peptide may be administered in a pharmaceutical composition.

In yet another embodiment of the present invention, there is disclosed a method for reducing the invasiveness of malignant cells, comprising administering to the malignant cells an E-domain peptide. In such embodiment, the E-domain peptide agent is preferably selected from the group consisting of: a trout E-domain peptide, an E-domain peptide homolog, and an E-domain peptide fusion protein, and more preferably is an E-domain peptide of a rainbow trout. Preferably, the trout E-domain peptide is selected from the group consisting of: Ea-2 domain peptide (SEQ ID NO:2) and Ea-4 domain peptide (SEQ ID NO:4). The E-domain peptide agent may be administered in a pharmaceutical composition.

And yet in another embodiment of the present invention, there is disclosed a method for reducing the invasiveness of malignant cells, comprising administering to the malignant cells a nucleic acid encoding an E-domain peptide agent. Preferably, the E-domain peptide agent is selected from the group consisting of: a trout E-domain peptide, an E-domain peptide homolog, and an E-domain peptide fusion protein, and more preferably is an E-domain peptide of a rainbow trout. Preferably, the trout E-domain peptide is selected from the group consisting of: Ea-2 domain peptide (SEQ ID NO:2), and Ea-4 domain peptide (SEQ ID NO:4). The nucleic acid encoding the E-domain peptide may be administered in a pharmaceutical composition.

The above-discussed and other features and advantages of the present invention will be appreciated and understood by those skilled in the art from the following detailed description and drawings.

BRIEF DESCRIPTION OF THE DRAWINGS

FIG. 7 is a table illustrating the effect of Ea-4-peptide on the invasion activity of HT-1080 cells on Matrigell.

Figure 1A:
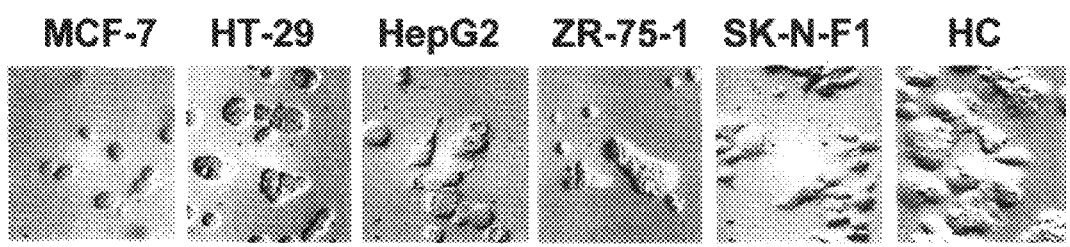
FIGS. 1A, 1B and 1C is a photomicrograph of human tumor cell lines [293GP, MCF-7, HT-29, HepG2, ZR-75-1, SK-N-F1 (human neuroblastoma cells) and Peoceliposis hepatoma cells (HC)] with and without treatment with Ea-4 peptide of trout pro-IGF-I or human IGF-I.

The E domain peptides of rainbow trout include the Ea-1 domain peptide, RSVRAQRHTDMPRTPKEVHQKNSS-RGNTGGRNYRM (SEQ ID NO, 1); the Ea-2 domain peptide, RSVRAQRHTDMPRTPKKPLSGNSHTSCK-EVHQKNSSRGNTGGRNYRM (SEQ 5 ID NO:2); the Ea-3 domain peptide, RSVRAQRHTDMPRTP-KVSTAVQSVDRGTERRTAQHPDKTKP-KKEVHQKNSSR GNTGGRNYRM (SEQ ID NO:3); and the Ea-4 domain peptide, RSVRAQRHTDMPRTP-KVSTAVQNVDRGTERRTAQHPDKTKT-KKKPLSGNSHT SCKEVHQKNSSRGNTGGRNYRM (SEQ ID NO:4). As described below, the Ea-2, Ea-3 and Ea-4 domain peptides have mitogenic activity on several types of cells, as shown by stimulation of increased incorporation of [$^3$H]-thymidine into the DNA of cells exposed to the E domain peptides, and/or by stimulation of increased total DNA content in cells exposed to the E domain peptides. In addition, the Ea-2 and Ea-4 domain peptides induce morphological change and cell attachment in cells exposed to the E domain peptides and grown in a serum-free medium. The Ea-4 domain peptide also prevented transformed cells and malignant tumor cells from forming colonies in a soft agar medium, thereby restoring the contact inhibition activity of the transformed (malignant) and tumor cells.

The invention takes advantage of these biological activities of the E domain peptides. In the methods of the invention, E domain peptides of a trout are used. As used herein, the term "E peptide" or "E domain peptide" refers to a peptide that forms an E domain of IGF-I of a trout. In a preferred embodiment, the trout is a rainbow trout, such as Onchorynchus species, and particularly *Onchorynchus mykiss*. In a particularly preferred embodiment, the E domain peptide is the Ea-1 (SEQ ID NO:1), Ea-2 (SEQ ID NO:2), Ea-3 (SEQ ID NO:3) or Ea-4 (SEQ ID NO:4) domain peptide of *Onchoiynchus mykiss*. The E domain peptides can be isolated from naturally-occurring sources, chemically synthesized or recombinantly produced.

The amino acid sequence of the E domain peptide can be that of the naturally-occurring protein or can comprise alterations therein. Such alterations include conservative or non-conservative amino acid substitutions, additions and deletions of one or more amino acids; however, such alterations should preserve at least one of the biological activities of the E domain peptide as described herein, i.e., the altered or mutant E domain peptide should be an active derivative of the naturally-occurring E domain peptide. For example, the mutation(s) can preferably preserve the mitogenic activity of the native E domain peptide, or the ability of the E domain peptide to induce morphological changes or cell attachment. The presence or absence of E domain biological activity or activities can be determined by various standard functional assays such as those described below in the Examples. Moreover, amino acids which are essential for the function of the E domain peptide can be identified by methods known in the art. Particularly useful methods include identification of conserved amino acids in the family or subfamily of IGF-I proteins, site-directed mutagenesis and alanine-scanning mutagenesis (for example, Cunningham and Wells, *Science* 244:1081–1085 (1989)), crystallization and nuclear magnetic resonance. Specifically, appropriate amino acid alterations can be made on the basis of several criteria, including hydrophobicity, basic or acidic character, charge, polarity, size, the presence or absence of a functional group (e.g., —SH or a glycosylation site), and aromatic character. Assignment of various amino acids to similar groups based on the properties above will be readily apparent to the skilled artisan; further appropriate amino acid changes can also be found in Bowie et al. (*Science* 247:1306–1310(1990)).

Peptides which are at least about 70% identical, preferably at least about 80% identical, and more preferably at least about 90% identical to the trout E domain peptides described herein can also be used, provided that the peptides have at least one of the biological activities of an E domain peptide, as described herein. Such peptides are referred to herein as "E domain peptide homologs".

The E domain peptide can also be part of a fusion protein comprising the amino acid sequence of an E domain peptide or an E domain peptide homolog, fused to an additional component. Additional components, such as radioisotopes and antigenic tags, can be selected to assist in the isolation or purification of the peptide or to extend the half life of the peptide; for example, a hexahistidine tag permits ready purification by nickel chromatography. A fusion protein comprising an E domain peptide is referred to herein as ar. "E domain peptide fusion protein".

The trout E domain peptides, E domain peptide homologs, and E domain peptide fusion proteins described herein are referred to collectively as "E domain peptide agents." In the methods of the invention, at least one E domain peptide agent is used; more than one E domain peptide agent can also be used. If more than one E domain peptide agent is used, the agents can be different types. For example, an E domain peptide and an E domain peptide homolog can be used concurrently, as can an E domain peptide homolog and an E domain peptide fusion protein. Alternatively or in addition, if more than one E domain peptide agent is used, the agents can be of the same type. For example, two E domain peptides, such as the Ea-2 domain peptide and the Ea-4 domain peptide, can be used concurrently.

DETAILED DESCRIPTION OF THE INVENTION

The present invention provides a method and compositions useful for reducing tumor growth and tumor cell invasiveness.

Novel biological activities are shown to be associated with E-peptides of the rainbow trout pro-IGF-I. In addition to mitogenic activity, trout pro-IGF-I Ea-2 and Ea-4-peptide possess activities including induction of morphological changes, enhancing cell attachment, restoring anchorage-dependent cell division behavior, eliminating anchorage independent cell division, and reducing the invasiveness of aggressive cancer cells. Further, in vivo studies conducted in the present inventor's laboratory demonstrates that tumors developed from the Ea-4-peptide treated ZR-75-1 cells in nude mice are substantially smaller than those developed from untreated cells. Since similar morphological changes have also been induced in a hepatoma cell line of *Peoceliposis lucida* (desert guppy) by treatment with the trout Ea-4-peptide, this rules out the possibility that the effect of trout pro-IGF-I E-peptides observed in human cancer cells is the consequence of artifact.

REPRESENTATIVE EXAMPLES

Cell Cultures Utilized In Studies

For routine maintenance of cell cultures, MCF-7 cells (ATCC, human breast cancer cells) and ZR75-1 cells (ATCC, human breast cancer cells) were cultured in F12/DMEM supplemented with 10% fetal bovine serum (FBS), and 10 ng/ml of insulin (Gibco-BRL, Rockville, Md.), HT-29 cells (ATCC, human colon cancer cells) in F12/DMEM (GIBCO/BRL) with 10% FBS, HepG2 cells (ATCC, human hepatoma cells) and 293GP cells (transformed human embryonic kidney cells provided by Dr. J. C. Burns at UCSD) in DMEM with high glucose, HC cells (*Peoceliposis lucida* hepatoma cells, provided by Dr. Larry Hightower at the University of Connecticut, Storrs, Conn., U.S.A.) in $CO_2$-independent medium and SK-N-F1 cells (ATCC, human neuroblastoma cells). Cells were incubated at 37° C. under a humidified atmosphere of 5% or 10% $CO_2$. All tissue culture media used in this study were purchased from Gibco-BRL (Rockville, Md.).

Example 1

Morphological Changes Induced by Ea-4-Peptide

Overview: To determine whether the Ea4-peptide may possess biological activities other than the mitogenic activity reported by Tian et al (1), oncogenic transformed or established cancer cells derived from human and fish (293GP, MCF-7, HT-29, HepG2, ZR-75-1, SK-N-F1, or HC cells) were challenged with the peptide and gross morphological changes recorded.

Methodology: Approximately $1-2\times10^5$ of MCF-7, HT-29, HepG2, 293GP, HC or SK-N-F1 cells re-suspended in their respective basal medium without fetal bovine serum (SF), were plated in a 6-well culture chamber. Prior to plating cells, an acid-washed coverslip was placed in each well of the culture chamber. Various amounts of the trout Ea-4-peptide (2.1 nM) or human IGF-I (hIGF-I, 2.5 nM) were added to each well and the cell cultures were incubated at 37° C. under a humidified atmosphere of 5% $CO_2$. Coverslips were removed from the culture chamber 24 h after initiation of the treatment and observed under an Olympic inverted microscope equipped with differential interference phase contrast (DIC) objective lenses (final magnification, 200×).

Figure 1B:
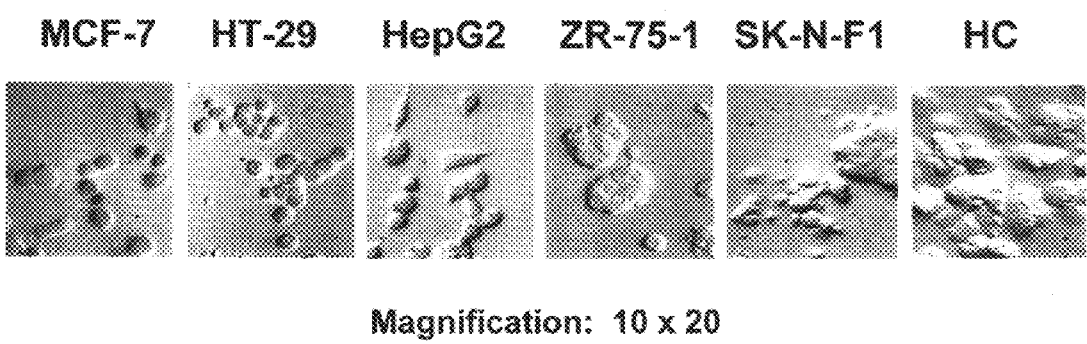
Figure 1C:
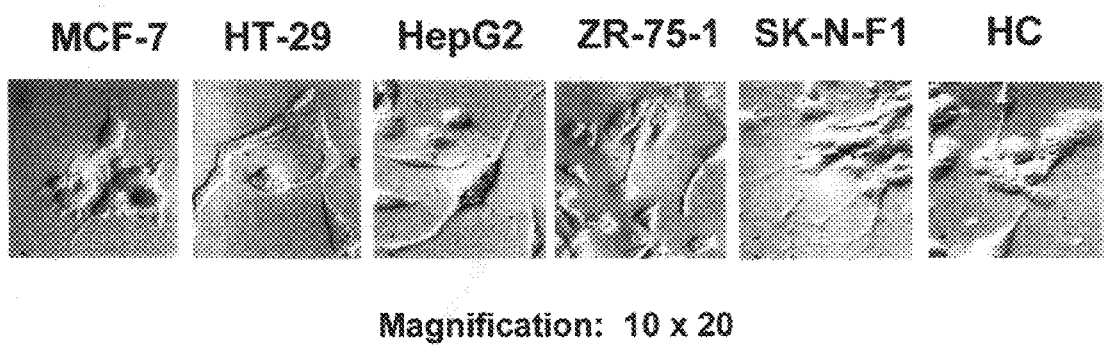

Results: FIG. 1 is a photomicrograph of human tumor cell lines [293GP, MCF-7, HT-29, HepG2, ZR-75-1, SK-N-F1 (human neuroblastoma cells) and Peoceliposis hepatoma cells (HC)] with and without treatment with Ea-4 peptide of trout pro-IGF-I or human IGF-I. As can be seen in FIG. 1, individual cells in the serum-free medium, with or without h-IGF-I treatment, exhibited rounded morphology and were loosely attached to the culture dish. Cells, however, treated with the Ea-4-peptide were flattened out and attached tightly to the culture dish. Furthermore, the Ea-4-peptide treated cells developed several pseudopodia-like structures (multiple processes) to establish contact with neighboring cells like that seen in non-transformed or non-malignant cells. After several days of culturing in the serum-free medium, cancer cells treated with or without hIGF-I grew into colonies, whereas those treated with Ea-4-peptide spread out in the culture dishes and grew into monolayers (data not shown). The latter are common characteristics exhibited by untransformed or non-malignant cells.

Example 2

Effect of Inhibition of Synthesis of RNA or Protein on Morphological Changes Induced by Trout Ea-4-Peptide Overview: The morphological changes induced by the Ea-4-peptide could be the result of direct interaction of the Ea-4-peptide with pre-existing proteins in the cell or with newly synthesized proteins induced by the Ea-4-peptide. To determine whether the morphological changes induced by Ea-4 peptide required synthesis of new proteins or RNA, tumorgenic cell-lines were treated with the peptide in and outside of the presence of known RNA synthesis inhibitors and protein synthesis inhibitors.

Methodology: 293GP and MCF-7 cells were cultured under the conditions described in above and then treated with 2.1 nM of the trout Ea-4-peptide. The cells were then treated with a-amanitin (10 μg/ml), an RNA synthesis inhibitor, or cycloheximide (1 μg/ml), a protein synthesis inhibitor. Twenty fours after initiation of treatment with the Ea-4-peptide and the inhibitors, cells are observed under an Olympic inverted microscope equipped with differential interference phase contrast (DIC) objective lenses (200× magnification).

Figure 3A:
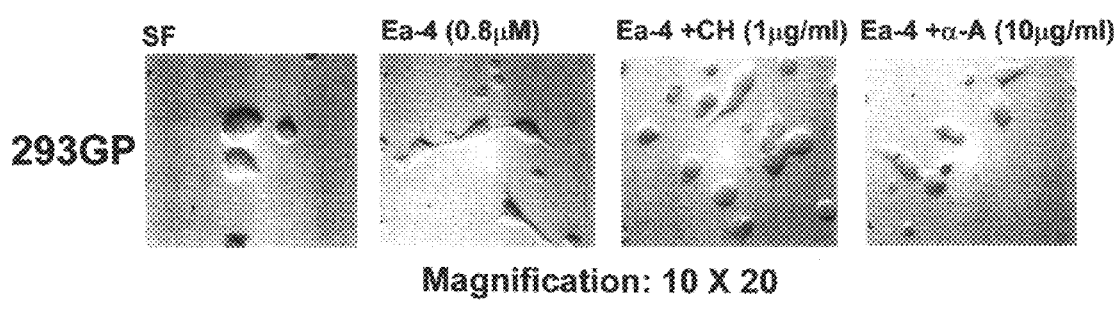
FIGS. 3A and 3B is a photomicrograph of oncogenic transformed/established tumor cell lines 293GP and MCF-7 cells cultured under control conditions alon, control conditions+α-aminitin, an RNA synthesis inhibitor, or control conditions+cycloheximide, a protein synthesis inhibitor.
Figure 3B:
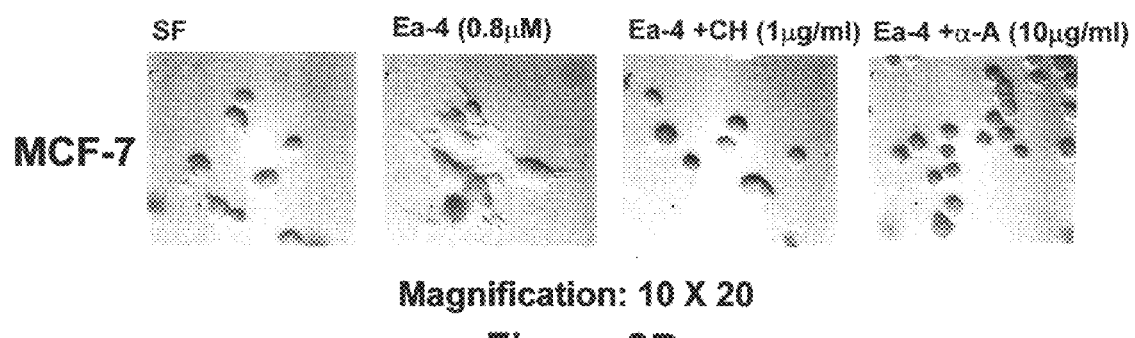

Results: FIG. 3 is a photomicrograph of oncogenic transformed/established tumor cell lines 293GP and MCF-7 cells cultured under control conditions alone, control conditions+α-aminitin, an RNA synthesis inhibitor, or control conditions +cycloheximide, a protein synthesis inhibitor. As shown in FIG. 3, the morphological changes in the 293GP and MCF-7 cells, induced by the Ea-4-peptide, were abolished by treatment with cycloheximide or α-aminitin. The viability of the inhibitor-treated cells was determined by the dye extrusion assay and the results showed that inhibitor-treated cells remain viable (data not shown). These results suggest that the morphological changes induced by the Ea-4-peptide may result from expression of genes that are inactivated during oncogenic transformation or tumor development since these experiments were conducted with oncogenic transformed or established tumor cells. The syntheses of new RNA and proteins appear to be required for the Ea-4-peptide induced morphological changes.

Example 3

Effect of Ea-2, Ea-3 and Ea-4 Peptides on Induction of Morphological Changes In ZR-75-1 and 293GP Cells Overview: A study was undertaken to determine if there was a differential effect of three of the known Ea-4-peptides of the rainbow trout on the induction of morphological changes.

Methodology: ZR-75-1 and 293GP cells were cultured in their respective basal medium following conditions described above. Twenty four hours after treatment with various concentrations of Ea-2 (SEQ ID NO:2), Ea-3 (SEQ ID NO:3) or Ea-4 (SEQ ID NO:4)-peptide, cells were observed under an Olympic inverted microscope equipped with differential interference phase contrast (DIC) objective lenses (200×magnification).

Figure 2A:
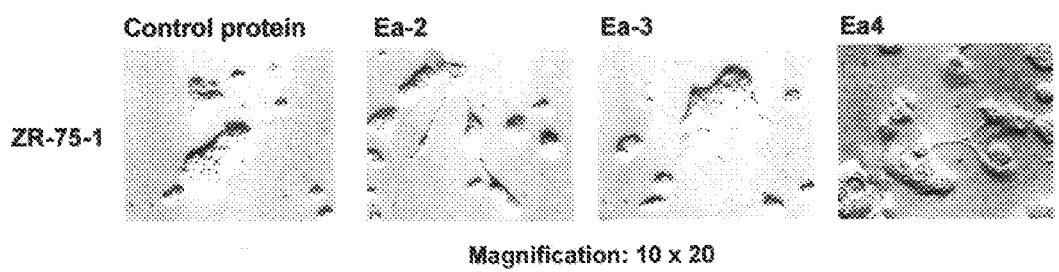
FIGS. 2A and 2B is a photomicrograph of oncogenic transformed/established tumor cell lines 293GP and ZR-75-1 cells cultured in basal medium for twenty-four hours and then treated with Ea-2-, Ea-3, or Ea-4-peptide.
Figure 2B:
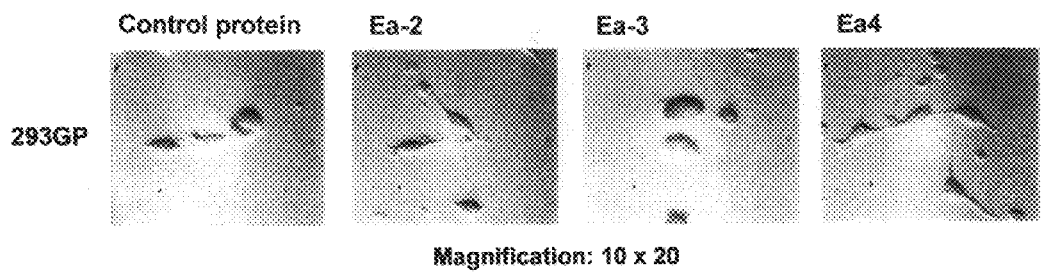
Figure 4:
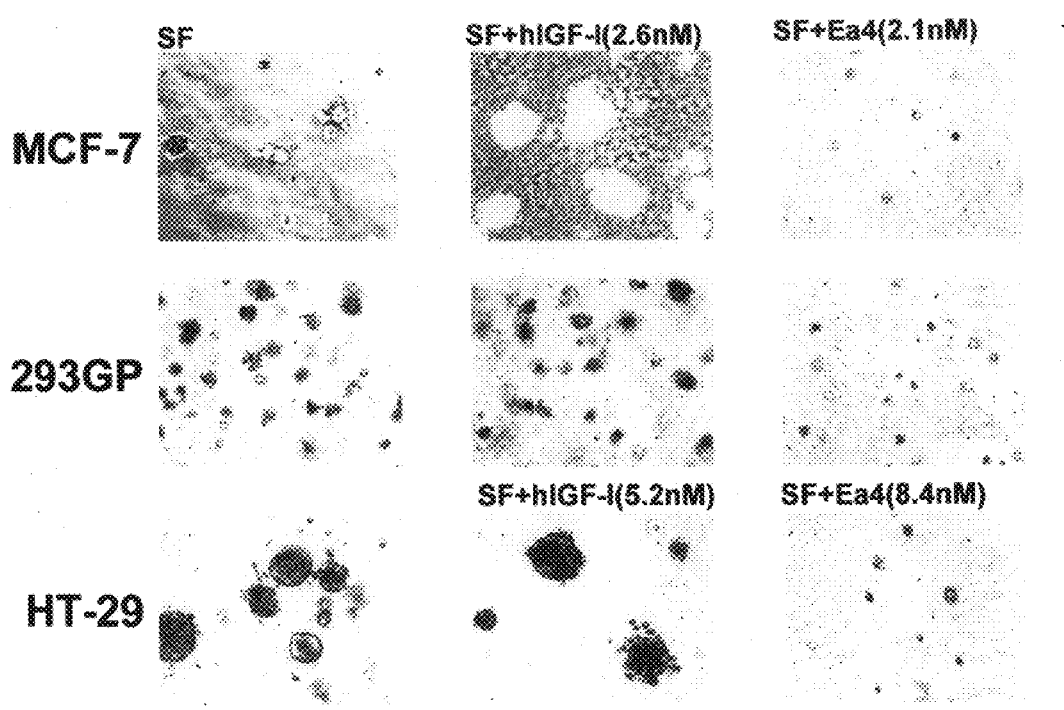
FIG. 4 is a photomicrograph of oncogenic transformed/established tumor cell lines 293GP, MCF-7 or HT-29 plated on basal medium containing 0.4% agar without fetal bovine serum and various concentrations of h-IGF-I or trout Ea-4-peptide.

Results: FIG. 2 is a photomicrograph of oncogenic transformed/established tumor cell lines 293GP and ZR-75-1 cells cultured in basal medium for twenty-four hours and then treated with Ea-2-, Ea-3, or Ea-4-peptide. Although both Ea-2- and Ea-4-peptides are able to induce morphological changes in 293GP or ZR-75-1 cells, the Ea-3 peptide fails to induce any visible morphological change under the identical culture conditions (FIG. 4). This observation suggests that the domain of the E-peptide responsible for the induction of morphological changes in the 293GP or ZR-75-1 is not present in the Ea-3-peptide (1).

Example 4

Effect of Ea-4-Peptide on Colony Formation Activity

Overview: An obvious change in the characteristics of normal cells after oncogenic transformation is the loss of contact inhibition and anchorage-dependent cell division behavior (10). This behavioral change in oncogenic transformed or cancer cells can be easily demonstrated in vitro by the colony formation assay in a semi-solid medium (11). Since treatment of oncogenic transformed cells or cancer cells with the Ea-4-peptide results in morphological change and increased cell attachment, it is conceivable that this protein may also affect the anchorage-independent cell division behavior of oncogenic transformed or cancer cells. To test this hypothesis, a colony formation assay was conducted following the methodology described by Yang (9).

Methodology: About $2 \times 10^4$ of MCF-7, HT-29 or 293GP cells at log phase were plated in their respective basal medium without FBS but containing 0.4% purified agar (Difco laboratories) and supplemented with various concentrations of hIGF-I (2.6 nM or 5.2 nM) or trout Ea-4-peptide (2.1 nM or 8.4 nM), in six-well culture chambers. After the medium was solidified, each well was overlaid with 1 ml of their respective medium supplemented with same concentration of hIGF-I or trout Ea-4-peptide. The plates were incubated at 37° C. in a humidified incubator with 5% $CO_2$ and examined daily under an inverted microscope for 2 weeks. Colonies were observed under an Olympic inverted microscope equipped with phase contrast objective lenses (40×magnification). The viability of cells at the conclusion of the experiment was confirmed by the dye extrusion assay with trypan blue.

Results: FIG. 4. is a photomicrograph of oncogenic transformed/established tumor cell lines 293GP, MCF-7 or HT-29 plated on basal medium containing 0.4% agar without fetal bovine serum and various concentrations of h-IGF-I or trout Ea-4-peptide. As shown in FIG. 4, visible colonies were developed from three transformed cell lines grown in a serum-free soft agar medium with or without hIGF-I treatment, but no colony developed from any of the three cell lines cultured in the serum-free medium supplemented with recombinant Ea-4-peptide. These results show that the Ea-4-peptide is able to restore the anchorage-dependent cell division in oncogenic transformed or tumor cells. Furthermore, it is of interest to note that hIGF-I promotes colony formation in this study. This observation is consistent with results reported by other investigators where hIGF-I stimulated the proliferation of tumor cells (12).

Example 5

Effect of Ea-4-Peptide Gene on Colony Formation Activity

Figure 5:
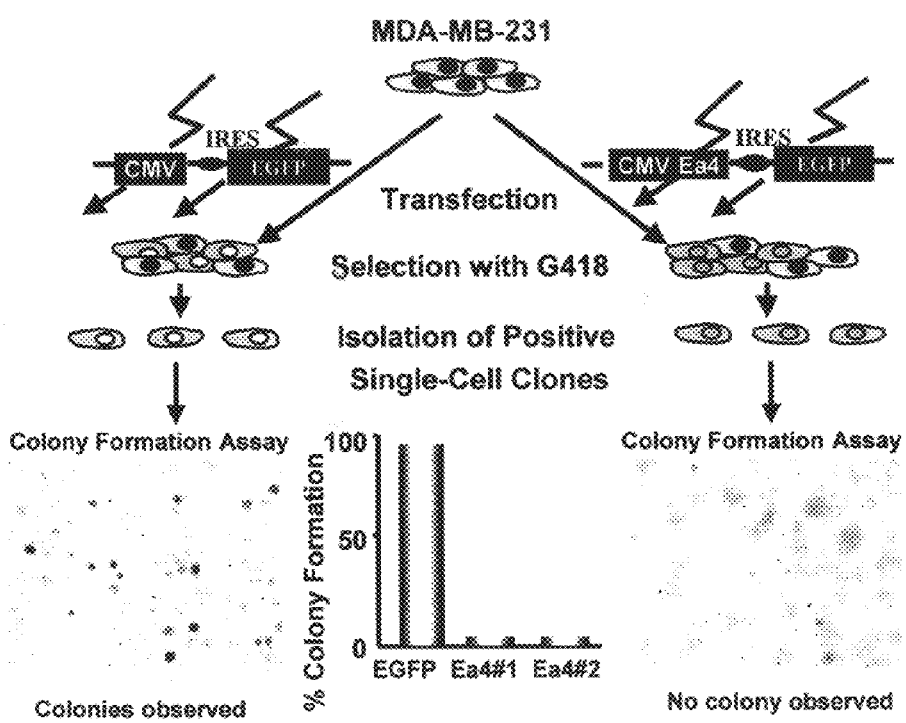
FIG. 5 is an illustration of a procedure undertaken to transfect a gene construct containing a green fluorescence gene (EGFP) or Ea-4 peptide gene and green fluorescence gene (EGFP) into MDA-MB-231 breast tumor cells, and a method for determining colony formation activity of the transfected Ea-4 positive clones from EGFP controls, and the photomicrographs of MDA-MB-231 breast tumor cells transfected with EGFP alone, and EGFP and Ea-4, with a graph interposed there between that indicates the relative colony formation under each scenario.

Overview: The effect of Ea-4-peptide gene on the colony formation activity of MDA-MB-231 cells was adjudged Methodology:. MDA-MB-231 breast tumor cells were transfected with a gene construct containing an Ea-4-peptide gene and a green fluorescence (EGFP) gene and permanent transformants isolated. Both Ea-4-peptide transformants and control cells are subjected to colony formation assay on a soft agar medium and colonies scored. FIG. 5 illustrates the procedure undertaken to transfect the gene construct and the method utilized to determine colony formation of the transfected Ea-4 positive clones as compared to EGFP controls.

Results: FIG. 5 comprises photomicrographs of MDA-MB-231 breast tumor cells transfected with EGFP alone, and EGFP and Ea-4, with a graph interposed there between that indicates the relative colony formation under each scenario. While numerous colonies are observed in EGFP control cells, no colony was observed in Ea-4-peptide transformed cells.

Example 6

The Effect of Ea-4-Peptide on Tumor Growth in Nude Mice

Overview: The effect of Ea-4-peptide gene on the tumor growth in nude mice was adjudged Methodology: About $1.3 \times 10^7$ ZR75-1 tumor cells, treated with trout Ea-4-peptide (70 μg) were injected into the back of nude mice (three sites per animal). Two types of controls were used: (i) mice injected with $1.3 \times 10^7$ ZR75-1 tumor cells treated with saline and (ii) mice injected with protein preparation that does not contain Ea4-peptide. Eighteen days after tumor cell injection, the size of tumors developed in each mouse was measured. All mice were sacrificed at day 51 and tumors excised for weight measurement.

Figure 6:
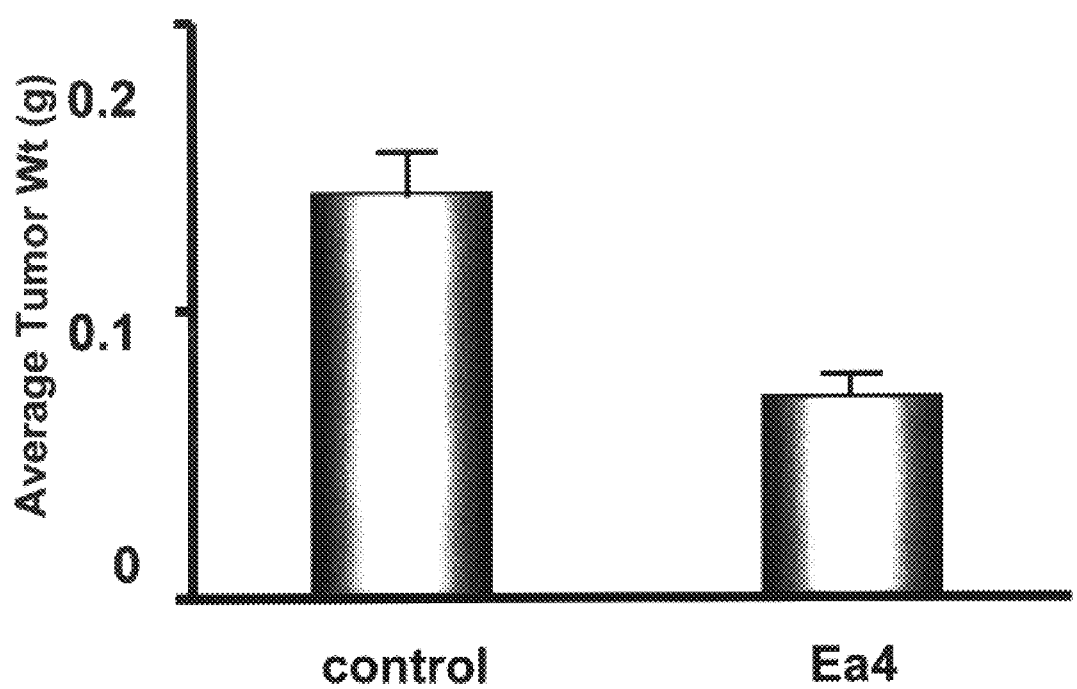
FIG. 6 is a graph illustrating the effect of Ea-4-peptide on tumor growth, induced by injection of ZR75-1 cells in nude mice.

Results: FIG. 6 is a graph illustrating the effect of Ea-4-peptide on tumor growth. The results clearly show that the tumors developed from ZR75-1 cells treated with trout Ea4-peptide were only half in size and weight when compared with tumors developed from control mice. Therefore, trout Ea-4-peptide can inhibit the growth of tumors.

Example 7

The Effect of Ea-4-Peptide on Metastatic Cancer Invasiveness

Overview: Another characteristic of cancer cells is their ability to invade normal tissues (metastasis) by migrating to other locations and colonization. The molecular events of metastasis have become more clear in recent years. These events involve the secretion of metaloproteases by tumor cells, digestion of basement membrane (invasion), and migration and colonization of cancer cells in new locations (13). This invasive behavior can be demonstrated by an in vitro invasion assay where the migration of cancer cells across the semi-solid Matrigel (proteins isolated from basement membranes) is measured. To investigate whether the Ea-4-peptide of trout pro-IGF-I can retard the invasive activity of cancer cells, an in vitro invasion assay was conducted in HT1080 cells, a known invasive cancer cell line, in the presence of Ea-4-peptide.

Methodology: Invasion assays were conducted in BIO-COAT MATRIGEL invasion chambers following the procedure provided by Becton Dickinson Labware (Bedford, Mass.; 40480 and 40481 guidelines). $1 \times 10^6$ of HT1080 cells (a known metastatic cancer cell line) in DMEM supplemented with 1.25% FBS, with or without various concentrations (4.2 and 8.4 nM) of the Ea-4 peptide, were plated in each insert of the Matrigel or control invasion chambers. The inserts were placed in the respective chambers containing DMEM medium supplemented with 10% FBS, and entire chambers were incubated at 37° C. under a humidified atmosphere of 5% $CO_2$ for 24 h. After removal of the non-invaded cells with cotton swabs, the invaded cells on the other side of the membranes were stained with the Diff-Quick™ stain (Becton Dickinson Labware, Bedford, Mass.) and observed under an Olympic inverted microscope (magnification, 200×).

Results: FIG. 7 is a table illustrating the effect of Ea-4-peptide on the invasion activity of HT-1080 cells on Matrigell. As shown in the table at FIG. 7, treatment of HT-1080 cells with Ea-4-peptide results in a dose-dependent reduction in the invasive activity of HT1080 cells. The addition of Ea-4 peptide to HT-1088 cells on Matrigell decreased the invasive activity of HT-1080 cells from 60% to 14%, a 4-fold reduction of the invasive activity. Ea-4-peptide can therefore stop the metastasis of tumor cells during the expansion of tumor development.

Example 8

Effect of Ea-4-Peptide on Attachment of Cells

Overview: To determine whether treatment of transformed cells with the Ea-4-peptide results in increased attachment of the cells to the culture dish.

Methodology: In the absence of fetal bovine serum, 293GP cells were cultured in a serum-free F12/DMEM supplemented with hIGF-I (2.6 nM) or Ea-4-peptide (2.1 nM), respectively. After one week, the culture medium was removed, and cells were rinsed twice with PBS, fresh PBS was added, and the culture plates were shaken 20 times manually. Extent of attachment was then determined.

Results: At the end of shaking, cells cultured in serum-free medium or serum-free medium supplemented with hIGF-I detached completely from the culture chamber while cells cultured in the serum free medium supplemented with Ea-4-peptide remained attached to the culture chamber. These results indicate that the Ea-4-peptide enhances the attachment of oncogenic transformed cells to the culture chamber, similar to the behavior exhibited by untransformed cells.

While the invention has been described with respect to preferred embodiments, those skilled in the art will readily appreciate that various changes and/or modifications can be made to the invention without departing from the spirit or scope of the invention as defined by the appended claims. All documents cited herein are incorporated in their entirety.

What is claimed is:

1. A method of inhibiting proliferation of malignant cells, comprising administering to the malignant cells at least one E-domain peptide from Insulin Growth-Like Factor-1 selected from the group consisting of trout Ea-2 and EA-4 domain peptides having the amino acid sequence of SEQ ID NOS: 2 or 4 and E-domain peptide fusion proteins having the amino acid sequences of SEQ ID NOS: 2 or 4.

2. The method of claim 1, wherein the E-domain peptide is an E-domain peptide of a rainbow trout.

3. The method of claim 2, wherein the trout E-domain peptide is selected from the group consisting of: Ea-2 domain peptide (SEQ ID NO: 2) and Ea-4 domain peptide (SEQ ID NO:4).

4. The method of claim 3, wherein the E-domain peptide is administered as a composition containing the E-domain peptide and a pharmaceutically acceptable carrier.

5. A method for reducing the invasiveness of malignant cells, comprising administering to the malignant cells composition containing an E-domain peptide from Insulin Growth Factor-Like 1 and a pharmaceutical carrier, wherein said E-domain peptide is a member selected from the group consisting of Ea-2 and Ea-4 domain peptides having the amino acid sequence of SEQ ID NOS: 2 or 4 and E-domain fusion proteins having the amino acid sequence of SEQ ID NOS: 2 or 4.

6. The method of claim 5, wherein the E-domain peptide is an E-domain peptide of a rainbow trout.

7. The method of claim 6, wherein the trout E-domain peptide is selected from the group consisting of: Ea-2 domain peptide (SEQ ID NO: 2) and Ea-4 domain peptide (SEQ ID NO: 4).

* * * * *

SEQUENCE LISTING

<160> NUMBER OF SEQ ID NOS: 6

<210> SEQ ID NO 1
<211> LENGTH: 35
<212> TYPE: PRT
<213> ORGANISM: Onchorhynchus mykiss

<400> SEQUENCE: 1

Arg Ser Val Arg Ala Gln Arg His Thr Asp Met Pro Arg Thr Pro Lys
1               5                   10                  15

Glu Val His Gln Lys Asn Ser Ser Arg Gly Asn Thr Gly Gly Arg Asn
            20                  25                  30

Tyr Arg Met
        35

<210> SEQ ID NO 2
<211> LENGTH: 47
<212> TYPE: PRT
<213> ORGANISM: Oncorhynchus mykiss

<400> SEQUENCE: 2

Arg Ser Val Arg Ala Gln Arg His Thr Asp Met Pro Arg Thr Pro Lys
1               5                   10                  15

Lys Pro Leu Ser Gly Asn Ser His Thr Ser Cys Lys Glu Val His Gln
            20                  25                  30

Lys Asn Ser Ser Arg Gly Asn Thr Gly Gly Arg Asn Tyr Arg Met
        35                  40                  45

<210> SEQ ID NO 3
<211> LENGTH: 62
<212> TYPE: PRT
<213> ORGANISM: Oncorhynchus mykiss

<400> SEQUENCE: 3

Arg Ser Val Arg Ala Gln Arg His Thr Asp Met Pro Arg Thr Pro Lys
1               5                   10                  15

Val Ser Thr Ala Val Gln Ser Val Asp Arg Gly Thr Glu Arg Arg Thr
            20                  25                  30

Ala Gln His Pro Asp Lys Thr Lys Pro Lys Lys Glu Val His Gln Lys
        35                  40                  45

Asn Ser Arg Gly Asn Thr Gly Gly Arg Asn Tyr Arg Met
    50                  55                  60

<210> SEQ ID NO 4
<211> LENGTH: 74
<212> TYPE: PRT
<213> ORGANISM: Oncorhynchus mykiss

<400> SEQUENCE: 4

Arg Ser Val Arg Ala Gln Arg His Thr Asp Met Pro Arg Thr Pro Lys
1               5                   10                  15

Val Ser Thr Ala Val Gln Asn Val Asp Arg Gly Thr Glu Arg Arg Thr
            20                  25                  30

Ala Gln His Pro Asp Lys Thr Lys Thr Lys Lys Pro Leu Ser Gly
        35                  40                  45

Asn Ser His Thr Ser Cys Lys Glu Val His Gln Lys Asn Ser Ser Arg
    50                  55                  60

Gly Asn Thr Gly Gly Arg Asn Tyr Arg Met

-continued

```
<210> SEQ ID NO 5
<211> LENGTH: 27
<212> TYPE: DNA
<213> ORGANISM: Artificial Sequence
<220> FEATURE:
<221> NAME/KEY: misc_feature
<223> OTHER INFORMATION: derived from Onchorhynchus mykiss

<400> SEQUENCE: 5
ctactacata tgcgctcagt gcgcgca                                        27

<210> SEQ ID NO 6
<211> LENGTH: 30
<212> TYPE: DNA
<213> ORGANISM: Artificial Sequence
<220> FEATURE:
<221> NAME/KEY: misc_feature
<223> OTHER INFORMATION: derived from Onchorhynchus mykiss

<400> SEQUENCE: 6
ctccccgata tcctacattc ggtagtttct                                     30
```